(12) United States Patent
Gindilis

(10) Patent No.: US 6,344,333 B2
(45) Date of Patent: *Feb. 5, 2002

(54) REAGENT-FREE IMMUNOASSAY MONITORING ELECTRODE ASSEMBLY

(75) Inventor: Andrei L. Gindilis, Mukilteo, WA (US)

(73) Assignee: Synectig Corporation, Denville, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/148,900

(22) Filed: Sep. 8, 1998

(51) Int. Cl.[7] .............................................. G01N 33/543
(52) U.S. Cl. ............................ 435/7.1; 422/56; 422/57; 422/58; 422/82.01; 422/82.02; 435/7.9; 435/7.93; 435/288; 435/291; 435/817; 436/518; 436/524; 436/525; 436/528; 436/544; 436/806; 436/807; 204/400; 204/403; 204/415
(58) Field of Search .......................... 422/56–58, 82.01, 422/82.02; 435/288, 7.1, 7.9, 7.93, 291, 817; 436/518, 524, 525, 528, 544, 806, 807; 204/400, 403, 415

(56) References Cited

U.S. PATENT DOCUMENTS 5,063,081 A * 11/1991 Cozzette et al.
5,281,539 A * 1/1994 Schramm
5,391,272 A * 2/1995 O'Daly et al.
5,698,083 A * 12/1997 Glass

OTHER PUBLICATIONS

Ghindilis et al. (1992). A new approach to the construction of potentiometric immunosensors. Biosensors and Bioelectrics. 7:301–304.*
Varfolomeev et al. (1996). Direct electron transfer effect biosensors. Biosensors and Bioelectronics, 11(9):864–871.*
Dzantiev et al. (1996). Electrochemical immunosensors for determination of the pesticides 2,4–dichlorophenoxyacetate and 2,4,5–trichlorophenoxyacetic acids. Biosensors and Bioelectronics. 11:179–185.*
Monroe (1986). Immunoselective electrodes. Immunoassay Technology. 2:57–70.*
Boitieux et al. (1981). Use of solid phase biochemistry for potentialmetric enzyme immunoassay of oestradiol–17b—preliminary report. Clinica Chinica Acta. 113:175–182.*
Yamamoto et al. (1978). Potentiometric investigations of antigen–antibody and enzyme–enzyme inhibitor reactions using chemically modified metal electrodes. J. Immunol. Methods. 22:309–317.*
Cooper et al. (1988). The nautre of biosensor technology. J. Biomed. Eng. 10:210–219.*
Ghindilis et al. (1996). Potentiometric biosensors for cholinesterase inhibitor analysis based on mediatorless bioelectrocatalysis. 11(9):873–880.*

* cited by examiner

Primary Examiner—Christopher L. Chin
(74) Attorney, Agent, or Firm—Elliot M. Olstein; Alan J. Grant

(57) ABSTRACT

The present invention relates to an apparatus to perform reagent-free assays, which apparatus utilizes an all solid probe having an enzyme label that acts on a substrate by obtaining electrons directly from the electrode by bioelectrocatalysis.

17 Claims, 4 Drawing Sheets

Electrocatalytic electrode
potential

Electrocatalytic electrode potential

Background electrode potential

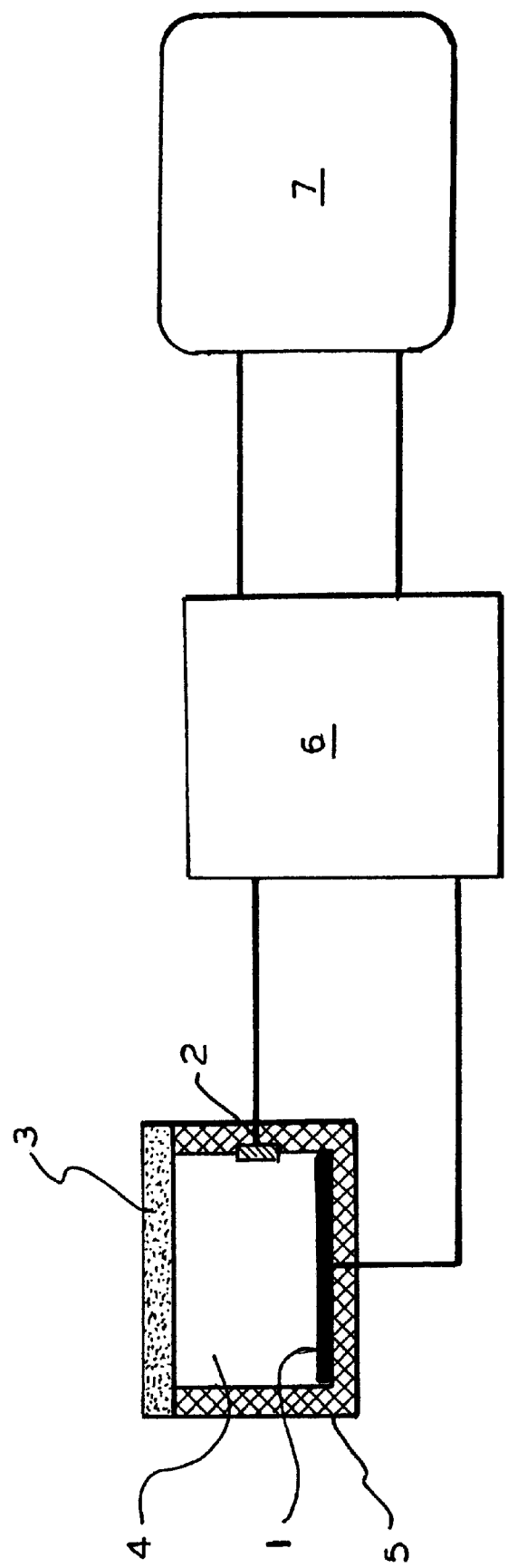
F I G. 2

REAGENT-FREE IMMUNOASSAY MONITORING ELECTRODE ASSEMBLY

The present invention relates to assays that employ an enzyme label or tag that acts on a substrate by obtaining electrons from an electrode (electrocatalysis) and an apparatus for use in such assays.

BACKGROUND OF THE INVENTION

Immunoassay techniques are based on the ability of antibodies to form complexes with the corresponding antigens or haptens. This property of highly specific molecular recognition of antigens by antibodies leads to high selectivity of assays based on immune principles. The high affinity of antigen-antibody interactions results in great sensitivity of immunoassay methods. The use of a label or indicator to verify that an antigen/antibody interaction has occurred is the basis for immunoassay methods.

Immunoassay techniques have been used mainly in clinical analyses and medical diagnostics. However, immunoassay applications in other areas such as environmental control, food quality control, etc. are expanding. Certain limitations in assaying techniques due to existing procedures have limited somewhat the expansion into such other areas.

In this respect, during the last few years a significant number of publications have dealt with non-conventional (alternative) immunoassay techniques designed to expand the accuracy or applicability of immunoassays. In most cases the development of alternative immunoassay techniques aims at improvements in performance of conventional immunoanalysis. Often such improvement attempts are directed to decreasing analysis times, increasing assay sensitivity, and simplifying and automating assay procedures.

For example, the utilization of enzymes able to catalyze electrochemical reactions by direct (mediatorless) mechanism (bioelectrocatalysis) would allow for the detection of immuno-interactions in real time. Such applications of bioelectrocatalysis in the development of immunosensors are based on the self-assembling or displacement of molecule/label complexes or "molecular transducers" on the surface of an electrode that has been modified by immunospecies that bind the complex. Ordinarily these immunospecies would be complimentary to the immunoconjugate which includes the electrocatalytically active enzyme-label.

Antigen immobilized on the electrode surface interacts with the enzyme-labeled antibody which results in the attachment of the enzyme to the electrode surface. Attachment of the electrocatalytic active enzyme on the electrode surface initiates, in the presence of a substrate, an electrocatalytic reaction. Therefore, the formation of an antigen-labeled antibody complex on the electrode surface is accompanied by an assembling of the molecular transducing layer. The rate of electron transfer can be limited by the efficiency of electrical connection between the enzyme-label and the electrode surface, which is already modified by the immobilized immunospecies.

A potentiometric immunosensor based on mediatorless bioelectrocatalysis has been utilized which employed laccase enzyme as an electrocatalyst-label. The electrocatalytic property of the enzyme in the reaction of oxygen electroreduction (reaction 1) allowed the detection of the biospecific interaction of a laccase-labeled receptor, or antibody, with a ligand modified electrode. Formation of a complex between the laccase labeled antibody and antigen on the electrode surface results in a considerable shift in electrode potential due to the catalytic reduction of over voltage. Analysis was performed in a competitive scheme, and a single measurement was made with 20 minutes. Such a potentiometric immunoassay does not require an electrochemically active mediator. The reaction substrates were atmospheric oxygen and electrons that were transferred directly from the electrode to the oxygen molecule via the active site of the enzyme. Insulin was used as a model analyte.

In the above immunoassay sensor, the electron which is the "second substrate" of enzymatic reaction can be captured by the enzyme-label only from the electrode surface. Therefore, only molecules intimately attached to the electrode surface generate electrochemical signal. The rate of attachment of electrocatalyst molecules to the electrode surface is proportional to the rate of formation of the immuno-complex on the electrode surface. The rate of attachment of electrocatalyst molecules to the electrode surface is proportional to the rate of formation of the immuno-complex on the electrode surface. The rate of immunointeraction on the electrode surface can be directly monitored by amperometric or potentiometric mode.

However, assays based on mediatorless bioelectrocatalysis are limited in that primarily one of the two assay procedures set forth below are utilized and only a single assay measurement may be taken before the electrode is regenerated or replaced by a new electrode. The two competitive assay procedures are:

(a) Competitive Immunoassay With an Initial Label-free Electrode—An electrode having no attached analyte/enzyme label is utilized as a starting point and a measured amount of analyte media along with a measured quantity of analyte/enzyme label are assayed by a competitive binding assay procedure. After maximum association with the electrode has occurred the amperometric or potentiometric measure result is compared to that of an electrode having 100% analyte/enzyme label associated. The difference in measurements corresponds proportionally to the amount of analyte in the media being assayed. and (b) Displacement Immunoassay With an Initial Label-loaded Electrode—An electrode having the maximum amount of attached analyte/enzyme label (a filly loaded electrode) is utilized as a starting point and a measured amount of analyte media is assayed by a competitive binding assay procedure. After maximum displacement of the analyte/enzyme label from the electrode by the analyte of the media has occurred the amperometric or potentiometric measure result is compared to that of the initial fully loaded electrode (having 100% analyte/enzyme label associated). The difference in measurements corresponds proportionally to the amount of analyte in the media being assayed.

In addition to the laccase enzyme label, the potentiometric immunosensor employing peroxidase as an electrocatalyst-label has also been developed. The basic principle is the same as for the laccase based immunosensor. The electrode surface is modified by an immobilized antigen (rabbit IgG). The peroxidase-antibody conjugate associates with the antigen on the electrode surface. Once added to the media, and on reaching the electrode surface, the antibody-conjugated peroxidase starts to catalyze the electro-reduction of hydrogen peroxide. This results in an increase (anodic shift) in the electrode potential.

Both the laccase and peroxidase label immunosensors based on bioelectrocatalytic detection (as discussed above) allow direct detection of immunointeraction in real time. However, these sensors must be regenerated or replaced (e.g., disposable sensors) after each measurement.

Accordingly, such immunoassay procedures do not allow continuous monitoring of the analyte. In addition, such procedures are a multi-stage process that result in a general complexity of analysis and require a highly qualified technician to conduct the assay.

Accordingly, there is a need for immunoassay procedures that can be continuous, particularly automatable procedures or procedures that do not require highly qualified technicians to conduct the assay.

SUMMARY OF THE INVENTION

An object of the present invention is to provide an improved bioelectrocatalysis immunoassay apparatus for detecting an analyte, the apparatus comprising a sensing device with an electrode, wherein the sensing device has the ability to monitor changes in the amount of analyte in a liquid without requiring regeneration or replacement of the electrode or of the reagents used in the assay. Preferably, the sensing device of the apparatus is capable of multiple intermittent and/or continuous immunoassay measurements of the same analyte without a requirement for regeneration or replacement of the electrode or other reagents.

In one aspect the apparatus is for detecting an analyte that is an antigen, antibody or hapten by use of a labeled detection compound that is labelled with an electrocatalytic enzyme, wherein the labeled detection compound is either the analyte or the binder for the analyte, and wherein the apparatus provides an electrode to which is permanently affixed (i) a binder for the analyte in the case wherein the labeled detection compound is a labeled analyte or (ii) the analyte in the case wherein the labeled detection compound is a labeled binder for the analyte. If such detection compound becomes closely associated with the electrode of the apparatus, the electrocatalytic enzyme label or tag will interact with the electrode to cause a detectable electrical change for the electrode. In one embodiment the analyte is the same antigen, antibody or hapten as the detection compound (wherein the detection compound is labeled with an electrocatalytic enzyme or tag) and some of the fixed amount of the labelled detection compound complex that is detectable by the electrode due to bioelectrocatalysis competes with the analyte for binding to the binder of the electrode. Alternatively, the binder on the electrode and the analyte are the same antigen, antibody or hapten and compete for binding to the detection compound that is labelled with the electrocatalytic enzyme.

In accordance with the above apparatus (depending upon whether the analyte is the same as the binder or the same as the detection compound) the analyte will bind to either the binder or to the detection compound. In either event, the amount of the detection compound that attaches to the binder is inversely proportional to the concentration of the analyte in the sample being analyzed. The amount of the detection compound which is bound to the binder of the electrode is indirectly measurable by bioelectrocatalysis and the amount of analyte which is present in the sample is therefore detectable by the amount of bioelectrocatalysis occurring at the electrode's surface. In each of the above cases (i.e., (i) when the binder and analyte are the same and (2) when the binder and the detection compound are the same, the electrode only transfers an electron to the label as a substrate when the labeled detection compound is attached to the binder affixed to the electrode. Therefore, a shift in potential or current, can be observed by the amount of labeled detection compound that binds to the binder on the electrode, which amount of labeled detection compound bound to the binder on the electrode is inversely proportional to the amount of analyte in the sample. When current is measured instead of potential at the electrode, the current is proportional to the amount of laccase label attached to the electrode. Measurement of potential is preferred since amperometric measurement of the electrode signal takes into consideration the surface area of the electrode and the density of the laccase label attached to the electrode. Thus, potential measures are usually more accurate, but sometimes amperometric measures are more accurate and should be used. The ordinary practicioner in this field would know when to use a particular electrode type. Thus, when the terms "potentiometric electrode" and "potentiometric assay" and the like are used in this application and claims the word "amperometric" may be substituted for "potentiometric".

A further object of the invention is to provide an improved bioelectrocatalysis immunoassay sensing device wherein the electrode is encased by a housing member comprising at least one porous or semi-porous surface, such as a semipermeable membrane, that is permeable for an analyte and impermeable to the labelled detection compound, preferably a detection compound that is labelled with an electrocatalytic enzyme. In a preferred aspect the sensing device comprises a particular quantity of the labelled detection compound which is enclosed within the housing member, which labelled detection compound may contact the electrode when the sensing device is placed in a liquid or gaseous medium and the at least one porous or semi-porous surface is impermeable to the labelled detection compound.

A preferred object of the invention is to provide an apparatus for immuno-determination of target analyte (antigen, antibody or hapten) in an analyte sample, where said apparatus comprises (a) a sensing device comprising:
  (i) a potentiometric working electrode at least one surface of which is located within said housing member, wherein said electrode is connected to a potentiometric measuring circuit and said electrode has the ability to provide an electron to an enzyme label which will deliver the electron to a first substrate for the enzyme label, and said electrode has permanently affixed to at least one of its surfaces a binder for at least a detection compound which is labelled with an electrocatalytic enzyme;
  (ii) a housing member comprising at least one surface that is permeable to an analyte and impermeable to the labelled detection compound, wherein the detection compound is a member selected from the group consisting of (a) a binder for the analyte (in the case where the binder on the electrode is the analyte) and (b) the analyte (in the case where the binder on the electrode is a binder for the analyte), and in each case the detection compound is labelled with an electrolytic enzyme or tag; and
  (iii) an internal media which is located within the housing member and which is a gel or liquid containing a pre-determined amount of labelled detection compound as herein above described, or capable of containing a pre-determined amount of the labelled detection compound; and
(b) an electrochemical reference electrode connected to a potentiometric measuring circuit, and wherein the internal media of (iii) or the analyte sample comprises a second substrate for the enzyme label or tag, such as oxygen. The analyte will either bind to the binder or to the detection compound.

In a preferred aspect, the apparatus further comprises at least one measuring device which is connected directly or indirectly to the sensing device and/or the reference electrode. Preferably, the at least one measuring device is a member selected from a digital voltmeter or other similar a measuring device. In one aspect said measuring device is interfaced with a personal computer as well as the sensing element and the electrochemical reference probe. In a preferred aspect, the measuring device is also connected to a member selected from (i) a signal recorder which is an X-T recorder, (ii) a microprocessor based data acquisition system with a digital display, and (iii) a personal computer.

Additionally, an object of this invention is provide a sensing device comprising an external housing with at least one semipermeable surface and having within the housing device at least one surface of a working electrode comprised of an electrode body made by electrochemically inert electro-conductive material modified by a binder immobilized on its surface which will bind to at least a detection compound which is labelled with an electrocatalytic enzyme, and the binder may be the same as the analyte or may be a binder for the analyte. In a preferred aspect, the binder is a binder for both the analyte and the labeled detection compound, whereby the binder will reversibly bind individually to the analyte or to the labelled detection compound which will each compete to be bound by the binder. Preferably, the detection compound is labelled with the laccase enzyme which can use oxygen and electrons from the electrode as substrates.

Another object of the invention is a sensing element which comprises (a) a potentiometric working electrode, (b) an external housing with at least one surface that is a semipermeable surface (such as a diffusion membrane) through which an analyte may diffuse and is impermeable to at least one detection compound which is labelled with an electrolytic enzyme or tag and the detection compound will bind to either the binder of the electrode, or to both the binder on the electrode and the analyte of the sample, and (c) an electrochemical reference electrode. In a preferred aspect the sensing element further comprises an internal media, which is a gel or liquid, and a fixed quantity of the labelled detection compound, or comprises a means for inserting a quantity of labelled detection compound and/or the internal media comprising a fixed quantity of the labelled detection compound.

Another object of the invention is to provide a portable biosensor capable of continuously detecting a target analyte in a wide range which operates in a continual potentiometric mode from which multiple potentiometric measurements are available that correspond to the amount of analyte present in a given sample being assayed.

In yet another aspect, an object of the present invention is to provide a method for intermittently or continuously conducting immunoassay measurements wherein a plurality of different measurements for an analyte are available for a single electrode without requiring regeneration of said electrode and other reagents. In particular, such object is accomplished by a method of determination a target analyte based on displacement activity of the target analyte and a potentiometric mode comprising the following steps:

(a) immersing of the intermediate and/or continuous bio-electrocatalysis immunoassay sensing element (described above) in a assay medium containing the target analyte, (b) allowing the target analyte of the assay medium to diffuse through the diffusion membrane of the sensing device and travel to the surface of the working electrode, (c) permitting an immuno-equilibrium to be established within the sensing device with respect to the amount of target analyte present in the assay medium due to displacement of some or all of a labelled detection compound from the binder on the surface of the electrode by the target analyte which target analyte becomes bound to the binder on the surface of the sensing element in the case where the detection compound is the same as the analyte or the target analyte becomes bound to the detection compound in the case where the detection compound is a binder for the analyte, (d) measuring at least one shift of the electrode potential caused by the displacement of some or all of the labeled detection compound from the electrode's surface and the resulting diminishment or absence of electrocatalytic properties caused by the label of detection compound, (e) determining the potentiometric sensor response which is proportional to the degree of displacement of the labeled detection compound from the binder on the surface of the working electrode caused by competitive binding of the target analyte, and (f) determining the concentration of the target analyte in the external media from the potentiometric sensor response as compared with the control electrochemical reference electrode.

In yet further aspect, an object of the present invention is to provide a method for intermittently or continuously conducting competitive immunoassay measurements wherein a plurality of different measurements are available for a single electrode without requiring regeneration of said electrode. In the situation where the amount of target analyte changes to become more or less concentrated in a continuous monitoring process, a competitive binding immunoassay can be utilized. In particular, such object is accomplished by a method of determination the variations in amount of a target analyte based on displacement activity of the enzyme-labeled detection compound (i.e., labeled analyte) or from a binder for the analyte and the detection compound which binder is on the working electrode and corresponding potentiometric responses to such attachment changes, which method comprises the following steps:

(a) immersing of the intermediate and/or continuous bio-electrocatalysis immunoassay sensing element (described above) in a assay medium which may vary continuously with respect to the concentration of the target analyte present, (b) allowing the target analyte of the assay medium to diffuse through the diffusion membrane of the sensing device and travel to the surface of the working electrode, (c) permitting an immuno-equilibrium to be established within the sensing device with respect to the amount of target analyte present in the assay medium due to (i) displacement of some or all of a labeled detection compound (e.g., labeled analyte) that is reversibly bound to a binder immobilized on the surface of the electrode by the target analyte which target analyte becomes reversibly bound to the binder immobilized on the surface of the sensing element upon displacing the labeled detection compound, or (ii) displacement of some of the reversibly bound target analyte from the binder on the surface of the electrode by some of the fixed amount of the labeled detection compound that is present within the sensing device due to a lowering of the concentration of the target analyte which causes a shift in its binding equilibrium and degree of binding with the binder on the surface of the electrode, (d) measuring at least one shift of the electrode potential caused by the displacement occurring on the surface of the working electrode of either the reversibly bound labeled detection compound or the reversibly bound target analyte and resulting changes in electrocatalytic properties occurring at the surface of the electrode, (e) determining the potentiometric sensor response which is proportional to said binding displacement on the surface of the working electrode, (f) determining changes in the concentration of the target analyte in the external media from changes in the potentiometric sensor response as compared with the control electrochemical reference electrode and prior measurements from the working electrode.

In accordance with one aspect of the invention, there is provided an assay procedure wherein a sample containing analyte (a substance to be determined) placed in contact with an electrode which supports a binder for the analyte, which binder has bound thereto a labeled form of the analyte in which the label is an electrocatalytic enzyme (an enzyme that acts on a substrate by obtaining electrons from the electrode) and wherein such electrode is also contacted with a substrate for such enzyme label. The analyte in the sample displaces some or all of the reversibly bound labeled analyte from the binder, with the amount of binding displacement being directly related to the amount of analyte in the sample. Displacement of labeled analyte results in a change in voltage between such electrode and a reference electrode and such change in voltage is a measure of the amount of analyte in the sample.

In a preferred embodiment, the electrode having supported thereon the binder having bound thereto a labeled analyte is present in a chamber which includes a member or wall which is permeable to analyte but which is impermeable to the enzyme labeled analyte.

The sensing element is comprised of an electrode made by electrochemically inert electroconductive material (such as different carbon based materials, gold, different electroconductive polymers) modified by immobilized binder (such as the analyte) that is directly attached to the surface of the electrode and may be the same as the analyte or as a detection compound.

BRIEF DESCRIPTION OF THE DRAWINGS

FIG. 2 illustrates an immunosensor apparatus according to the invention comprising an electrochemical working electrode 1; an electrochemical reference electrode 2; the diffusion membrane 3 which separates working electrode 1 from the external media; the internal media 4 which may be a liquid or gel containing a substrate for an enzyme-label as shown in FIG. 1A; an external housing member 5 which fixes together the electrochemical working electrode 1, the electrochemical electrode 2, the diffusion membrane 3, the measuring device (the electrochemical interface) 6 which may be described as a digital voltmeter or an interface to microprocessor which measuring device is connected to the sensing element comprising the electrochemical working electrode 1 and the supporting electrochemical reference electrode 2, and signal recorder 7 which signal recorder may be described as an X-T recorder, a microprocessor based data acquisition system with digital display, or a personal computer.

DESCRIPTION OF SPECIFIC EMBODIMENTS

Figure 1A:
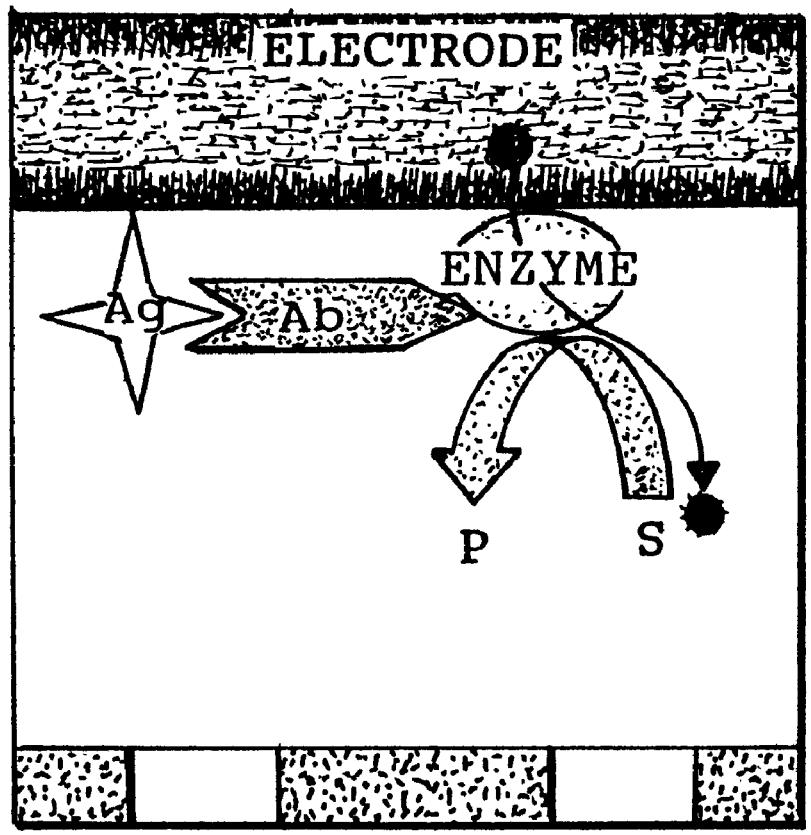
FIG. 1A illustrates an electron transfer at the surface of an electrode. The electrode has an antigen (marked "Ag") affixed to the electrode as its support and a labelled antibody/enzyme complex (marked "Ab" and "Enzyme") is attached to the affixed antigen. Due to the proximity of the enzyme to the electrode an electron is transferred to the substrate and electrocatalytically the electrode potential is changed by such electron transfer. Also shown in the drawing, by discontinuous lines and a rough raised surface is a semipermeable membrane across which an antigen may be diffused.
Figure 1B:
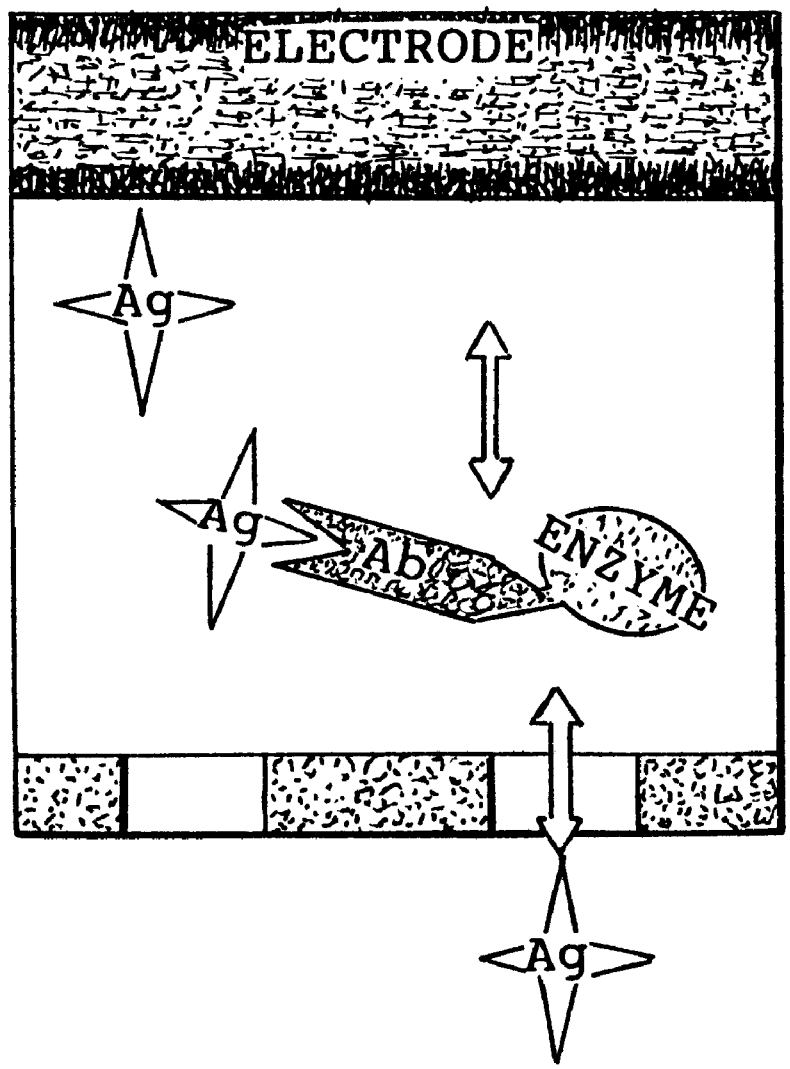
FIG. 1B illustrates a background electrode potential when the antigen (marked "Ag") which is affixed to the electrode is not linked to a labelled antibody/enzyme complex (marked "Ab" and "Enzyme") is attached to the affixed antigen. When the enzyme is in near proximity to the electrode an electron is transferred to the substrate and electrocatalytically the electrode potential is changed by such electron transfer. However, when the labeled antibody/enzyme complex becomes displaced (as shown in this drawing) and the enzyme is distanced from the electrode, no catalytic electron transfer occurs. Also shown in the drawing, by discontinuous lines and a rough raised surface is a semipermeable membrane across which an antigen may be diffused. A double arrow shows one such opening through which an antigen (analyte) can diffuse, but across which the antibody/enzyme complex cannot move.
Figure 3:
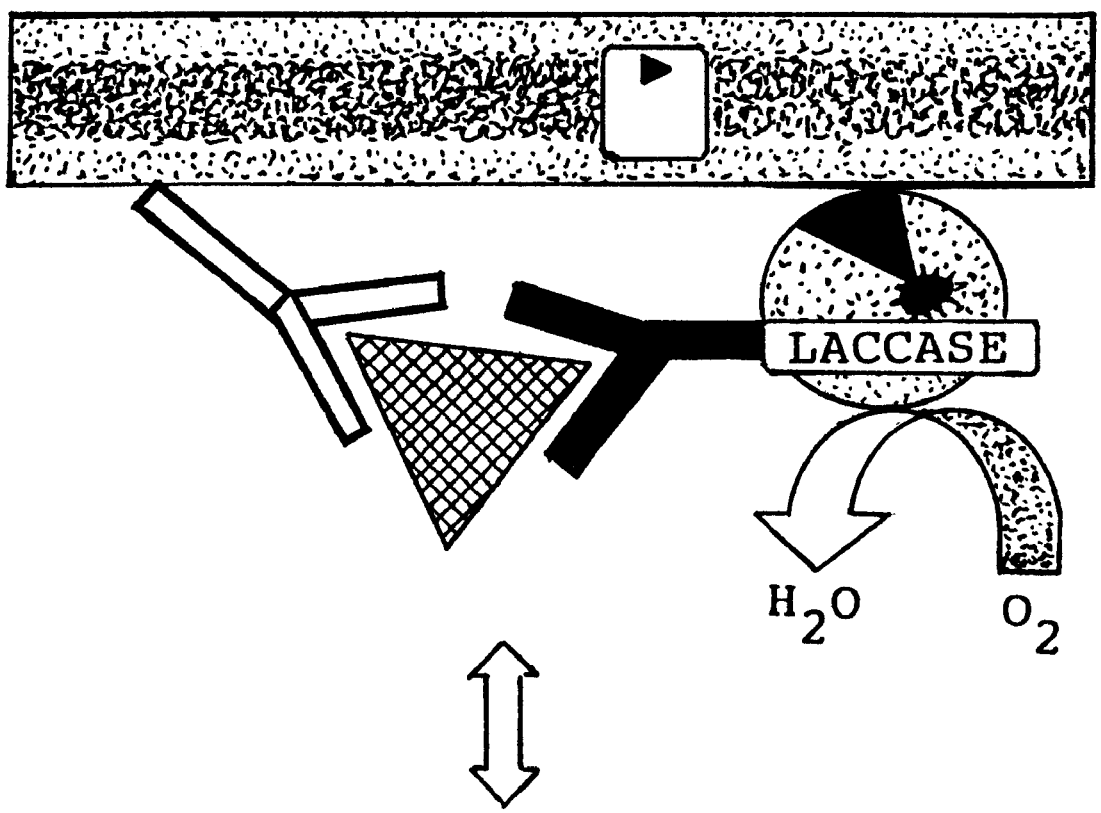
FIG. 3 is a shematic illustrating continuous immunoassay monitoring. In the presence of the analyte in the external media, the analyte diffuses through the membrane and forms a complex with an increase in potential. A decrease in the analyte concentration in the external media results in dissociation of the complex and leads to a decrease in the electrode potential.

The present invention provides an alternative approach to the development of immunosensors and is associated with bio-electrocatalytic detection of the reversibly displacement of a labeled detection compound that is reversibly bound to a binder (which binder is an analyte or a compound which will bind to the analyte) on an electrode surface, by free target analyte which will either bind to the binder on the surface of the electrode or compete with the binder for binding to the detection compound. In this case, the electrode is separated from the external media by porous membrane permeable for analyte and impermeable to higher molecular weight compounds such as the enzyme-labeled detection compound. Therefore, the labeled detection compound does not diffuse to the external media. A decrease in the concentration of target analyte in external media results in a new (target analyte)/(labeled detection compound) ratio and a new equilibrium with respect to how much of the enzyme-labeled detection compound is bound to the binder on the electrode. Such a decrease leads to release of analyte that is bound to either the binder or to the detection compound and to the re-binding of some labeled detection compound to the binder on the surface of the electrode. Therefore, continuous monitoring of the concentration of the analyte in a sample source is allowed (FIG. 1).

As shown in FIG. 2, the working electrode 1 serves for potentiometric measurement. It consists of an electroconductive material modified by the immobilized analyte. The reference electrochemical electrode 2 can be fixed inside the inert body 5 or be immersed into it together with sensing element. It can be represented by high impedance voltmeter or by interface which converts voltage signal to the format suitable for acquisition by microprocessor or personal computer. The signal recorder 7 serves to measure and visualize the initial rate of the increase of the electrode potential of the sensing element. It can be represented by simply X-T recorder, or by microprocessor based digital data acquisition system, or by personal computer supported with special software.

The advantage of the sensing device having a semipermeable membrane lies in its potential to provide continuous on line monitoring of analyte. The ability of the sensing device to detect analyte over a wide concentration range allows its use for on-line measurements of concentration for different analytes. FIG. 1 presents the overall scheme of the electrode function.

The working electrode is represented by an electroconductive highly dispersed material such as flat or dispersed carbon, graphite, carbon black, conductive dispersed pyrolytic products, conductive metal oxides, metal and metal powders, semiconductor materials, dispersed conductive polymers with binders (analytes or corresponding antibodies, antigens, or haptens for such analytes) that are immobilized on the surface of the electrode material.

The liquids used in the invention are water, buffer solutions, and aqueous sample diluents. Preferred liquids are buffer solutions such as phosphate buffered saline, borate buffered saline, acetate buffered saline, TRIS saline and the same buffer solutions containing detergents such as Tween, Triton etc. in different concentrations.

The enzyme-labels used in the invention are electrocatalytically active oxidoreductases represented but not limited by laccase (substrate oxygen); lactate dehydrogenase (substrate lactate); horseradish peroxidase, cytochrome c peroxidase, fungal peroxidases, lactoperoxidase, microperoxidase, chloroperoxidase (substrate hydrogen peroxide); hydrogenase (substrates hydrogen, proton); D-fructose dehydrogenase (substrate fructose), methylamine dehydrogenase (substrate methylamine); flavocytochrome c552 (substrate sulfide); succinate dehydrogenase (substrates succinate, fumarate); fumarate reductase (substrate fumarate); alcohol dehydrogenase (substrate ethanol); D-gluconate dehydrogenase (substrate gluconate); cellobiose dehydrogenase (substrate cellobiose); and ascorbate oxidase (substrate oxygen).

In a preferred aspect, the invention relates to immunoelectrochemical analysis employing laccase as the enzyme label. Laccase possesses strong electrocatalytic properties in that it can catalyze the electroreduction of oxygen (Berezin et al., Doklady Phys. Chem., 240:455 (1978, translated from Russian):

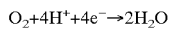

$$O_2 + 4H^+ + 4e^- \rightarrow 2H_2O$$

When laccase is utilized as the enzyme label the donor substrate is an electron moving directly from the an electrode which is in the proximity of the laccase enzyme and the second substrate is molecular oxygen.

The ability of the enzyme laccase to catalyze electroreduction of oxygen via a direct mechanism allows the detection of the biospecific interaction of a laccase-labeled receptor, or antibody, with a ligand-modified electrode. The potential established on the electrode coated with immobilized laccase is close to the equilibrium oxygen potential, and the shift in potential occurring in the presence of the immobilized enzyme can be as high as 400 mV. The bioaffinity interaction occurring on the electrode surface can therefore be determined by using a laccase-labeled bioconjugate. Formation of a complex between the laccase-labeled antibody and the antigen on the electrode surface results in a considerable (>300 mV) change in the electrode potential.

The change in electrode potential is due to the transfer of electrons directly form the electrode as a reaction substrate for laccase which react with the other substrate for laccase which is atmospheric oxygen, in that electrons are transferred directly from the electrode to the active site of the enzyme label. A composite carbon material containing a polyethyleneimine-based polymer can be used to eliminate nonspecific interactions between the reaction components and the electrode surface.

The potentiometric detection of an analyte does not depend on the electrode surface area. The electrode response is a function of the fraction of electrode surface that is covered by the electro-active label (laccase). This fact opens a possibility for miniaturization immuno-electrodes without effecting of their sensitivity. One of the important advantages of the bio-electrocatalytic detection approach in immunoassay is associated with the fact that the reaction does not involve low molecular weight substrates (except dissolved oxygen).

Several general practical advantages of the potentiometric immuno-sensors according to the invention can be summarized in five engineering issues: (i) potentiometric detection has a potential for a great degree of miniaturization of sensing elements; (ii) the manufacturing procedure of the sensing elements can easily be adapted for mass production being compatible with techniques such as screen-printing or ink-jet dispensing; (iii) it is possible to design low cost and thus, disposable sensing elements; (iv) the measuring equipment is simple consisting of a high impedance voltmeter.

In a preferred aspect, the invention provides a potentiometric immunosensor based on mediatorless bioelectrocatalysis that utilizes the laccase enzyme as an electrocatalyst-label. The electrocatalytic property of the enzyme in the reaction of oxygen electroreduction (reaction 1) allows the detection of the bio-specific interaction of a laccase-labeled receptor, or antibody, with a ligand modified electrode. Analysis was performed in a competitive scheme, and a single measurement was made within 20 minutes. Such a potentiometric immunoassay does not require an electrochemically active mediator. The reaction substrates are atmospheric oxygen and electrons that are transferred directly from the electrode to the oxygen molecule via the active site of the enzyme. Insulin may be used as a model analyte as illustrated by the examples below. Furthermore, a higher rate of electrode potential shift can be achieved by employing a high concentration of immuno-conjugate. A competition for binding with immobilized immuno-species for high concentration of immuno-conjugate can require a relatively high concentration of the analyte.

In one aspect of the invention the laccase enzyme label is bound to a binder (antibody, antigen or hapten, that is referred to above as a detection compound) for an analyte which detection compound is also bound by a binder on the electrode. The analyte will cause the enzyme label/detection compound to disassociate from the binder on the electrode and bind to the analyte to cause a change in potential of the electrode. Depending upon dynamic changes in the concentration of analyte that moves across the semipermeable membrane of the sensor which contains the enzyme label/ ligand and electrode, differing measurements of electrode potential are observed. For example, at higher concentrations of analyte more of the enzyme label/detection compound is disassociated from the electrode to bind to the analyte and at lower concentrations of the analyte more of the enzyme label/detection compound binds to the binder on the electrode. Since measurements in the increase or decrease in electrode potential can be made simultaneously with the biospecific interaction of the affinity components on the electrode surface, continuous measurements can be performed in the kinetic mode. This also allows for a significant reduction in analysis time since the rate of change in potential can be utilized to determine the changes in concentration as well as equilibrium measurements of potential.

In general, the amplitude of signals produced by working electrodes according to the invention is determined by the extent to which the electrode surface is coated with laccase-conjugated molecules, and not by the total amount of conjugated laccase bound to the electrode. A carbon composite can be used as an electrode material which possess a considerably large effective surface area, but higher sensitivity can be attained by the use of an electrode materials with a lower, or low, effective surface. The pH of the assay solution must be high enough to promote antigen-antibody complex formation. At the same time, it should not exceed the optimal value for the enzymatic activity, which is the case of laccase activity is about pH 5.5, but may exceed the optimal value for laccase activity somewhat. For example, an increase in pH above 5.5 when using laccase can result in a sharp decrease in the rate of potential change in the presence of the laccase-antibody conjugate, but may be as high as 6.5 where laccase from Coriolus sp. still retains 30–50% of maximal activity. Since laccase from different sources may differ in pH for their optimium activity, a laccase may be selected from a particular source when a particular optimal pH is desired. For example, laccase from certain fungi has a pH optimal activity near 7.0. Electrodes according to the invention, as described above do not have changes in the increase of the electrode potential over the temperature range of 30° C.–37° C., and dry IgG-modified electrodes will generally retain their activity during storage for at least 2 months at 4° C.

In another aspect the invention provides a method and apparatus for reagentless immunoassay is described, in that no reagent beyond the self-contained sensor apparatus is required and the self-contained sensor apparatus may be used for multiple measurements.

In a preferred embodiment of the invention the apparatus comprises an immunosensor have the general immunosensor design shown in FIG. 2, which includes the working electrode 1; the reference electrochemical electrode 2; a diffusion membrane which separates the working electrode 1 from the external media; the internal media 4 which is liquid or gel containing a substrate for an enzyme-label; an external housing member 5 which fixes together the working electrode 1, the electrochemical reference electrode 2, the diffusion membrane 3, the measuring device (the electrochemical interface) 6 which is a digital voltmeter or an interface to microprocessor which is connected to the sensing element and the supporting electrochemical probe 2, and signal recorder 7 which is an X-T recorder, microprocessor based data acquisition system with digital display, or personal computer. The working electrode 1 serves for potentiometric measurement. It consists of an electro-conductive material modified by the immobilized analyte. The supporting electrochemical reference electrode 2 can be fixed inside the external housing member 5 or be immersed into it together with the sensing element. It can be represented by high impedance voltmeter or by interface which converts voltage signal to the format suitable for acquisition by microprocessor or personal computer. The signal recorder 7 serves to measure and visualize the initial rate of the increase of the electrode potential of the sensing element. It can be represented by simply X-T recorder, or by microprocessor based digital data acquisition system, or by personal computer that is set to record and analyze the measurement results.

The above described apparatus may have multiple electrodes where the different electrodes are for different analytes. Thus, multiple analytes in a single sample may be analyzed for by utilizing the multiple electrodes.

Further, a Sandwich Assay Scheme can be used for continuous immunoassy monitoring. In the case where both primary and secondary (labeled) antibody are low affinity antibodies, the formation of a complex Ab1-Analtye-Ab2-Laccase may be reversable.

Having described the invention, the following non-limiting examples are given to illustrate specific techniques and applications of the principles of the invention. which can be used to carry out the invention. These specific examples are for illustrative purposes only and are not intended to limit the scope of the invention described in this application.

EXAMPLE 1

Preparation of a Laccase Enzyme Conjugate

Laccase from Coriolus sp. was obtained as described by Ghindilis et al., Biochemistry (translated from Russian: Biokhimiya) 53:635–639 (1988). Pig insulin was obtained as a commercial product (for example, Sigma, St. Louis, Mo., U.S.A.). The laccase-insulin conjugate was synthesized by using the general procedure of Nakane et al., J. Hist. and Cyto. Chem., 22 1084–1091 (1974) for the preparation of peroxidase conjugates. This procedure was modified as follows: a solution of NaIO was added to the solution of laccase in distilled water (1 mg ml$^{-1}$) to give a final concentration of 1.0 M. The mixture was incubated for 30 minutes, in the dark, at 18–22° C., and dialyzed against 0.1M sodium acetate buffer, pH 4.5 at 4° C. for 14–16 hours. Insulin was gradually added to the enzyme solution to give a molar ratio of 3:2. The mixture was incubated for 3 hours at 18–22° C. The pH of the reaction medium was maintained between 8.8 and 9.0. The conjugate obtained was dialyzed against 0.1 M phosphate buffer, pH 6.5, at 4° C., for 16–18 hours, and stored in 50% glycerol at −18° C.

EXAMPLE 2

Preparation of a Working Electrode

Graphite Ink, EXP 741801, obtained by Ercon (Wareham, Mass.), was deposited on a plastic strip (2×30 mm) and then dried at room temperature for 14–16 h. The electrode body was then encapsulated with fast dry enamel 720, obtained from Maybeline Inc. (New York, N.Y.). The tips of the electrode (2×2 mm) remained non-encapsulated to serve as a working electrode surface and as a connector to the electrical circuit. The electrode was then pretreated, by forced polarization, in a three electrode electrochemical cell under an electrode potential of −0.8 V versus an Ag/AgCl reference electrode for 20 min. A solution of monoclonal anti-insulin antibodies (20 ug/ml) in phosphate buffer saline (PBS) was then placed onto the working tip of the electrode and dried to achieve immobilization by physical absorption. Monoclonal antibodies were developed by Biocon Inc. (Rockville, Md.), from the ATCC HB127 hybridoma line obtained from ATTC (Rockville, Md.). The electrode was then incubated in a solution of trypsin inhibitor (0.1 mg/ml) in PBS to block free sites of non-specific binding for 4 h at room temperature. The electrode was then pre-incubated in the solution of laccase-insulin conjugate (0.1 mg/ml) in 0.1 M phosphate buffer, pH 6.2, containing 1 mg/ml human serum albumin (HSA) at 37 C., for 16 h, to achieve an attachment of the laccase-insulin conjugate to the electrode surface.

EXAMPLE 3

Analysis of Analyte Insulin Solution with a Working Electrode

The electrode was then placed into the sensing apparatus, as described in FIG. 2. The internal medium of the housing member contained a solution of laccase-insulin conjugate (5 ug/ml) in 0.1 M phosphate buffer, pH 6.2, containing 1 mg/ml HSA. The sensing apparatus was then placed in a contact with an external media (0.1 M phosphate buffere, pH 6.2, containing 1 mg/ml HAS) containing insulin analyte.

Atmospheric oxygen, which is a substrate for laccase, diffuses to the internal media through the external media. The potential of the working electrode, in the absence of insulin in the external media (antibody/laccase complex is bound to insulin that is affixed to the electrode) was close to $O_2/H_2O$ potential and was about 350 mV (vs Ag/AgCl electrode). The addition of insulin into the external media resulted in a shift of the potential towards the background carbon electrode potential (100 mV). The potential change was proportional to the concentration of insulin in the external media in a wide range of insulin concentrations.

As a reference, an Ag/AgCl electrode was used. Potential changes were measured by means of a high impedance voltmeter.

What is claimed is:

1. An apparatus for immuno-determination of a target analyte in an analyte sample, wherein said target analyte is selected from the group consisting of an antigen, an antibody and a hapten, and wherein said apparatus comprises a sensing device comprising:
   (i) a single potentiometric working electrode at least one surface of which is located within a housing member, wherein said electrode is connected to a potentiometric measuring circuit and said electrode has the ability to provide an electron to an enzyme label which delivers the electron to a first substrate for the enzyme label, and said electrode has affixed to at least one of its surfaces a binder for at least a labeled detection compound which is labeled with an electrocatalytic enzyme;
   (ii) a housing member comprising at least one surface that is permeable to an analyte and impermeable to the labeled detection compound, wherein the detection compound is a member selected from the group consisting of (a) a binder for the analyte when the binder on the electrode is the analyte and (b) the analyte when the binder on the electrode is a binder for the analyte, and wherein the detection compound is labeled with an electrocatalytic enzyme or tag; and
   (iii) an internal medium located within the housing member and wherein said medium is a member selected from a gel and a liquid and wherein said medium contains a pre-determined amount of a labeled detection compound; and
   (iv) an electrochemical reference electrode connected to a potentiometric measuring circuit,
wherein either said internal medium or the analyte sample comprises a second substrate for the enzyme label and the analyte binds to one of either the binder on said working electrode or the detection compound.

2. An apparatus according to claim 1 wherein the analyte will bind to the binder on said working electrode.

3. An apparatus according to claim 1, wherein the analyte will bind to the detection compound.

4. An apparatus according to claim 1, further comprising at least one measuring device which is connected directly or indirectly to a member of the group consisting of (a) the sensing device, (b) the reference electrode, and (c) both (a) and (b).

5. An apparatus according to claim 4, wherein the at least one measuring device for determining electrical changes of the electrode is a digital voltmeter.

6. An apparatus according to claim 4, wherein said measuring device is interfaced with a personal computer as well as the sensing element and the electrochemical reference probe.

7. An apparatus according to claim 6, wherein the measuring device is also connected to a member selected from the group consisting of (i) a signal recorder which is an X-T recorder, (ii) a microprocessor based data acquisition system with a digital display, and (iii) a personal computer.

8. The apparatus of claim 1, wherein said second substrate for the enzyme label or tag is oxygen.

9. A continuous immunosensor for determining the concentration or amount of an analyte in a sample, said sensing device comprising a single working electrode and an external housing with at least one semipermeable surface and having within the housing at least one surface of said single working electrode comprised of an electrode body made by electrochemically inert electro-conductive material modified by a binder immobilized on at least one of its surfaces which will bind to at least a detection compound that is labelled with an electrocatalytic enzyme, wherein the binder may be the same as the analyte or may be a binder for the analyte.

10. A sensing device according to claim 9, wherein the binder immoblized on at least working electrode is a binder for both the analyte and the labeled detection compound, and the binder will reversibly bind individually to the analyte or to the labelled detection compound to permit each to compete to be bound by the binder.

11. A sensing device according to claim 9, wherein the binder immobilized on at least one surface of the working electrode will bind to a labeled detection compound wherein the label is the laccase enzyme which can use oxygen and electrons from the electrode as substrates.

12. A sensing device according to claim 9, further comprising a member selected from the group consisting of:
   (a) an internal medium, which is a gel or liquid, and a fixed quantity of the labeled detection compound, and
   (b) a means for introducing into said medium a quantity of a member selected from the group consisting of (i) a labeled detection compound, (ii) an internal medium and (iii) both (i) and (ii).

13. A sensing device according to claim 12, wherein said sensing device is a portable biosensor that is capable of continuously detecting a target analyte which operates in a continual potentiometric mode from which multiple potentiometric measurements are available that correspond to the amount of analyte present in a given sample being assayed.

14. An apparatus for multiple determinations of a target analyte in a sample without requiring electrode regeneration, said apparatus comprising a housing that comprises:
   (i) at least one surface of a potentiometric working electrode connected to a potentiometric measuring circuit wherein said electrode has affixed to said surface a binder for at least one detection compound that is bound to an electrocatalytic enzyme and wherein in the presence of the target analyte said electrode provides an electron to said enzyme which then delivers an electron to a substrate of said enzyme, (ii) at least one surface that is both permeable to an analyte to be determined and impermeable to the detection compound of (a), wherein the detection compound is a member selected from the group consisting of a binder for the analyte when the binder on the electrode is the analyte and an analyte when the binder on the electrode is a binder for the analyte, (iii) an internal medium selected from the group consisting of a gel and a liquid wherein said medium contains a pre-determined amount of said labeled detection compound and an effective amount of said substrate; and (iv) an electrochemical reference electrode connected to a potentiometric measuring circuit, wherein only one said potentiometric working electrode is required for determination of said target analyte.

15. The apparatus of claim 14 wherein said detection compound is an antibody.

16. The apparatus of claim 14 wherein said target analyte is a molecule that reacts with the antibody of claim 15.

17. The apparatus of claim 14 wherein the binder on said working electrode binds the target analyte.

* * * * *

UNITED STATES PATENT AND TRADEMARK OFFICE
CERTIFICATE OF CORRECTION

PATENT NO.   : 6,344,333 B2                                              Page 1 of 1
DATED        : February 5, 2002
INVENTOR(S)  : Andrei L. Gindilis It is certified that error appears in the above-identified patent and that said Letters Patent is hereby corrected as shown below:

Column 2,
Line 42, "filly" should read -- fully --

Column 5,
Line 60, "a" should read -- an --

Column 6,
Line 44, "a" should read -- an --

Column 9,
Line 50, "an" should be deleted

Column 13,
Line 15, "antiabody" should read -- antibody --

Signed and Sealed this

Seventh Day of January, 2003

JAMES E. ROGAN
*Director of the United States Patent and Trademark Office*